(12) United States Patent
Niazi

(10) Patent No.: US 6,365,198 B1
(45) Date of Patent: Apr. 2, 2002

(54) PHARMACEUTICAL PREPARATION FOR THE TREATMENT OF GASTROINTESTINAL ULCERS AND HEMORRHOIDS

(75) Inventor: Sarfaraz K. Niazi, Deerfield, IL (US)

(73) Assignee: Gulf Pharmaceutical Industries (AE)

( * ) Notice: Subject to any disclaimer, the term of this patent is extended or adjusted under 35 U.S.C. 154(b) by 0 days.

(21) Appl. No.: 09/681,147

(22) Filed: Jan. 28, 2001

(51) Int. Cl.⁷ .......................... A01K 65/00; A61K 35/78
(52) U.S. Cl. ................................................. 424/725
(58) Field of Search ........................................ 424/725

(56) References Cited

U.S. PATENT DOCUMENTS

| | | | | |
|---|---|---|---|---|
| 1,383,896 A | * | 1/1921 | Wood et al. | |
| 1,890,596 A | * | 12/1932 | Zographos | |
| 3,062,716 A | * | 11/1962 | Montandraud | |
| 3,464,972 A | * | 9/1969 | Rocher | |
| 3,534,102 A | * | 10/1970 | Waldstein | |
| 3,594,473 A | * | 7/1971 | Hunger et al. | |
| 3,781,424 A | * | 12/1973 | Ponvert | |
| 3,935,310 A | * | 1/1976 | Homan | |
| 4,118,480 A | * | 10/1978 | Williams | |
| 4,169,143 A | * | 9/1979 | Haimowitz | |
| 4,202,825 A | * | 5/1980 | Taya | |
| 4,265,887 A | * | 5/1981 | Breskman | |
| 4,626,433 A | * | 12/1986 | Gold | |
| 4,732,760 A | * | 3/1988 | Iga et al. | |
| 4,761,285 A | * | 8/1988 | Vasiliou et al. | |
| 4,945,084 A | * | 7/1990 | Packman | |
| 4,985,257 A | * | 1/1991 | Verde | |
| 5,002,767 A | * | 3/1991 | Masse | |
| 5,196,405 A | * | 3/1993 | Oakman | |
| 5,234,914 A | * | 8/1993 | Gallina | |
| 5,266,571 A | * | 11/1993 | Amer | |
| 5,403,867 A | * | 4/1995 | Okumura | |
| 5,405,608 A | * | 4/1995 | Xu | |
| 5,562,906 A | * | 10/1996 | Terry et al. | |
| 5,591,436 A | * | 1/1997 | Pruthi | |
| 5,736,584 A | * | 4/1998 | Kunkel | |
| 5,747,462 A | * | 5/1998 | Feuntes | |
| 5,869,059 A | * | 2/1999 | Garza | |
| 6,030,978 A | * | 2/2000 | Kim et al. | |
| 6,048,533 A | * | 4/2000 | Nguyen | |
| 6,086,882 A | * | 7/2000 | Wambebe | |
| 6,117,868 A | * | 9/2000 | Priffmann | |

* cited by examiner

*Primary Examiner*—Jean C. Witz
*Assistant Examiner*—Brett Ozga

(57) ABSTRACT

A pharmaceutical preparation for the treatment of gastrointestinal ulcers and hemorrhoids in humans and animals and a method of preparation for this composition are provided here. The preferred composition consists of an alcoholic extract of Huangqin, Huanglian, Huangbo, Opuntia and Pheretima dissolved in vegetable oil from where alcohol is essentially removed by evaporation. The composition is then packaged in a soft gelatin capsule for oral administration or mixed with wax to make an ointment suitable for rectal administration.

6 Claims, No Drawings

PHARMACEUTICAL PREPARATION FOR THE TREATMENT OF GASTROINTESTINAL ULCERS AND HEMORRHOIDS

BACKGROUND OF INVENTION

This invention relates to a pharmaceutical preparation mainly for treating gastrointestinal wounds, ulcers and rectal inflammation conditions such as hemorrhoids. An alcoholic extract of natural ingredients in dried powdered state consisting of Huangqin (baikal skullcap), Huanglian (rhizome of Chinese goldthread or rhizoma Coptidis), Huangbo (cortex phellodendri), Pheretima (dilong) and Cactus (opuntia ficus indica) is used in an oily medium such that the quantity of each ingredient in its dried form represents less than 2% of the final amount of preparation. In the foregoing assertion, efforts have been made to find a suitable palliative and/or curative agent for the treatment of gastrointestinal ulcer conditions and hemorrhoids from medicinal plants and other natural ingredients.

Peptic ulcer is defined as a benign lesion of gastric or duodenal mucosa occurring at a site where the mucosal epithelium is exposed to acid and pepsin. It is a gastrointestinal problem that has been prevalent throughout the world population. It is estimated that approximately 10% of most populations globally will develop severe peptic ulcer conditions at some time during their lifetime. The lesions occur at all ages and affect both sexes. It is estimated that at least five million people suffer from active peptic ulcers each year, and approximately 350,000 to 500,000 new cases are diagnosed annually in the U.S. alone. More than 600,000 patients are hospitalized in the U.S. each year for severe episodes. In approximately one-third of these cases serious complications occur, including intestinal obstruction, upper gastrointestinal hemorrhage and perforation. Furthermore, each year, over 6,000 deaths in the U.S. are directly caused by ulcer disorders. In addition, peptic ulcer conditions have been implicated as an indirect contributing factor in an additional 11,000 deaths each year.

The occurrence of the disease has been associated with over-indulgence, inappropriate habits, anxiety and stress. Considerable energy and resources have been expended towards relieving symptoms of peptic ulcer, which usually manifests as an excruciating pain, especially in the upper abdomen. Peptic ulceration reflects an imbalance between the aggressive action of acid peptic secretions and the defensive forces that protect the mucosa. Gastric ulcers result from lowered defensive mechanisms and duodenal ulcers are the consequence of the destructive action of increased acid-peptic secretions.

Duodenal ulcers occur when gastric mucosa secretes substantial amounts of acid. Although some patients with duodenal ulcers have normal levels of acid secretion, on the average they are hyperchlorhydric. Gastric acid has two phases: a cephalic phase (vagally mediated) in which direct cholinergic stimulation of parietal cells induces gastrin release from the antrum, and a less powerful antral phase when food enters the stomach, causing liberation of more gastrin from the antral mucosa. Evidence that patients with duodenal ulcers have increased parietal cell mass also suggests a genetic predisposition even though experimental data indicate that parental cell hyperplasia can be acquired.

Gastric ulceration results from lowering of the gastric mucosal resistance. Principal among the defensive influences is mucous secretion. The increased frequency of gastric ulcers with advancing age might be compatible with progressive inability to secrete a protective layer of mucous. Chronic gastritis is a frequent concomitant of gastric ulcer, is associated with impaired mucous secretion and is also age-related. In experimental animals, it has been demonstrated that protein depletion, avitaminoses and general malnutrition increase the susceptibility to gastric ulceration.

The symptoms evoked by peptic ulcers are exceedingly variable; some ulcers being virtually asymptomatic. Nausea and vomiting may be produced by either duodenal or gastric ulcers, but particularly by the latter. The most consistent manifestation is epigastric pain described variably as burning, gnawing or boring. Classically, the duodenal ulcer pain becomes most severe two or three hours after the last meal and persists until food or antacids relieve it. For this reason, the pain recurs in the middle of the night and requires a glass of milk or antacid for its relief. Such episodic pain may last for weeks or months only to abate, usually with regulated dietary regimen and therapy. Recurrence is often triggered by dietary indiscretions or stress and is usually very rapid and sometimes dramatic, presenting with hemorrhage or perforation. Death from peptic ulcer is usually due to bleeding or perforation. In addition, a high proportion of patients who die or whose ulcers bleed or perforate have no warning signals.

In the past, chronic gastritis with prolonged dyspeptic symptoms in the upper stomach, the peptic ulcer, duodenal ulcer and ventral ulcer with pain in the upper stomach after meals or epigastric pain on empty stomach were a syndrome with unclear etiology. Its pathogenesis had not been clarified in detail. Generally, it can still be said today that there is no peptic ulcer without proteolytic gastric acid. Differential-diagnostic measures usually succeed in differentiating the peptic formation of ulcers from psychogenic gastrointestinal malfunctions. The final diagnosis depends on X-ray results.

For a long time, neutralization of gastric acid secretion with antacids and H2-receptor antagonists, have provided the only relief from the pains of peptic ulcer. The treatment modalities have historically included treatment based on administering antacids, such as magnesium or aluminum compounds, calcium carbonates, alkaline bismuth salts, e.g. bismuth aluminate, colloidal bismuth salts. A high relapse rate of over 80% and side effects, such as the rebound effect of acid secretion, deposits of aluminum and bismuth salts in the tissue to bismuth nephropathy, and bismuth encephalopathy forced the medical field to pursue new paths. The selective proximal vagotomy with surgical exclusion of the appropriate vagus branches or the acid-producing stomach sections in the case of relapsing stomach duodenal ulcers was another medical path that usually went nowhere. The relapse rate usually did not change with this serious surgical procedure. In acid secretion, $H_2$-receptors are involved. The introduction of the $H_2$-receptor antagonists cimetidine (Tagamet®) in 1977, and then ranitidine (Zantac®, Zostril®) represented a milestone in medicinal ulcer therapy. This led to rapid pain elimination with the healing of duodenal and ventral ulcers. Side effects of long-term therapy, such as infectious diarrhea, persistent hypergastrinemia with germ settlements on the antacid stomach lumen and nitrosamine formation, had to be accepted. Despite progress in acute therapy and the short-term prophylaxis of peptic lesions, the course of ulcers and the relapse rate has not been influenced by the $H_2$-receptor antagonists. The currently most potent molecule in the stemming of gastric acid is omeprazol and the newer generation pentaprazol. This category of proton pump inhibitors specifically blocks the $H^+/K^{30}$ adenosinetriphosphatases (ATP) of the mucosa of the stomach and thus hinders acid secretion. A suspected disadvantage is that, under permanent hypergastrinemia during Omeprazol therapy, a hyperplasia of neuroendocrine cells occurs and can lead to carcinoid tumors. The high effectiveness compared to the $H_2$-receptor antagonists, however, led to shorter treatment times at lower dosage (20 mg/day). The relapse rate remained unchanged.

Marshall et al. succeeded in 1983–1985 to prove the connection between the infection and gastritis through the rediscovery and ability to cultivate the germ *Campylobacter pylori* and through an oral infection in a self-test. This way the actual pathogenic factor of the ulcer was recognized. Initially, the germ was gained from biopsies of the antrum and corpus mucous membrane. In vitro cultivation did not succeed until later. According to examinations conducted by C. S. Goodwin, in Perth, Australia, the spiral-shaped *Campylobacter pylori* has little in common with other Campylobacter types (different fat composition, different enzyme metabolism, different genetic set-up). Therefore, it had to be renamed *Helicobacter pylori*. A spiral bent gram-negative germ, rods with lophotric flagellate, so-called clusters. Culturing is successful from stomach biopsies (antrum) on accumulation and selective media under micro aerobic conditions of 90% $N_2$, 5% $CO_2$, 5% $O_2$ for 3–4 days. Identification succeeds through additional proof of the enzymes oxidase, catalase, and urease. The germ is able to break down carbamide into ammonia in order to survive in an alkaline environment (cloud) in the acidic environment of the stomach. *Helicobacter pylori* only occur in humans and are transmitted fecal-orally. The pathogen infects and settles in the mucosa of the stomach. *Helicobacter heilmanni*, a variation of *Helicobacter pylori*, can be found in nearly all cats, dogs, and pigs. It can be passed on to humans. Infected people can develop disorders ranging from ulcers to stomach carcinomas. Due to the flagellated clusters, *Helicobacter pylori* is particularly mobile and excels through increased adherence to surface cells of the stomach epithelium. The mucous membrane is attacked by proteases of the germ. Vacuolizing cytokinin, which destroys the epithelium cells, is released. With the ELISA test, *Helicobacter pylori* IgG antibody levels can be proven over an extended period of time, even after the infection has subsided. This immune reaction leads in turn to tissue damage. After the infection, an acute B-gastritis type develops. If left untreated, the gastritis becomes chronic, and duodenal and stomach ulcers occur. This can then develop into an adenocarcinoma of the stomach. The World Health Organization (WHO) has included *Helicobacter pylori* into Category 4-Cancerogenes. The germ is to be interpreted as a resistance-weakening factor, which promotes early digestion of the mucosa of the stomach through the hydrochloricacidic proteolytically active gastric juice.

The evidence linking *Helicobacter pylori* with benign gastric ulcer is less convincing than duodenal ulcer. However, the consensus now is that the organism is probably important in the pathogenesis of 70% of gastric ulcers not attributable to the use of non-steroidal anti-inflammatory drugs (NSAIDS). The stomach's infection with the germ *Helicobacter pylori* is one of the most frequent infectious diseases in the world; in developing countries, more than 80% of the population is already infected with *Helicobacter pylori* during the childhood.

The modern ulcer therapy has two goals: alleviation of pain and to prevent complications and relapse rate. Antibiotics combination therapies include dual therapy with amoxacillin and omeprazole or triple therapy using bismuth, amoxcillin and metronidazole. Other modalities have utilized clarithromycin also.

The U.S. Pat. No. 6,117,868 to Pfirrmann describes a method and composition for the treatment of infectious gastrointestinal ulcer disease or infectious gastritis disease of microbially infected gastrointestinal tissue in a mammal involves administration of an antimicrobial amount of an antimicrobial medicament which is cell wall constituent-inactivating by chemical reaction with cell wall constituents, endotoxin non-releasing, exotoxin-inactivating or a combination thereof.

The U.S. Pat. No. 6,086,882 to Wambebe et al describes a phytochemical composition for management of peptic ulcer conditions in humans. The composition is a hot water extract of powdered *Indigofera arrecta* plant leaves.

The U.S. Pat. No. 4,732,760 to Iga, et al., is for a curative and preventive agent for ulcers of digestive organs comprising as the main constituent an active component having anti-ulcer activity derived from a hot-water, an alcohol or a water-alcohol mixed solution extract of cassia buds.

Inflammation, itching, and ulcerations characterize various diseases of the anorectic region of the human body. The anorectic region is generally comprised of the anus, rectum, and lower colon. In particular, hemorrhoids or piles are a common ailment of the anorectic region, and may be internally or externally located in the anorectic area. Notwithstanding their location, veins in the anorectic area become inflamed and frequently result in itching. The causes of hemorrhoids include predisposing causes such as erect posture, heredity, occupation and diet, constipation, diarrhea, pregnancy, anal infection, pelvic tumors, rectal carcinoma, cardiac failure, portal hypertension, vomiting and physical exertion.

Presently, there are millions of people around the world who suffer from hemorrhoids. A common condition, characterized by a mass of dilated tortuous veins in swollen tissue situated at the anal margin, hemorrhoids can be a source of extreme discomfort and pain to both men and women. Depending on the severity of the condition, there are various treatments and medical procedures, which are presently used to alleviate the pain or to remove hemorrhoid veins and swollen tissue. People suffering from minor hemorrhoids are ordinarily advised to use laxatives or stool softeners to reduce pain. Additionally, less severe cases are typically treated with topical ointments, such as petroleum jelly based products, to lubricate and, in some instances, numb the inflamed hemorrhoid mass. In more severe cases, it may be necessary to reduce pain and inflammation by injection of corticosteroid drugs or other medicinal drugs having the effect of reducing swelling and pain. Otherwise, banding may be required in order to push the hemorrhoids back into the rectal cavity. All of these treatment methods are generally useful to reduce the pain and discomfort of hemorrhoids. However, all of these treatment methods set forth above provide only temporary relief and must be repeated during and throughout flare-ups of the hemorrhoid condition.

The most severe cases of hemorrhoids often require cryosurgery or a hemorrhoidectomy to surgically remove the hemorrhoids. These procedures, while generally effective, are painful and considerably expensive. For this reason, surgical removal of hemorrhoids is a last resort performed only on those patients having severe, chronic hemorrhoid flare-ups.

Further, the treatment of hemorrhoids is complicated by the fact that during defecation, the fecal mass stretches, tears and irritates the already inflamed and swollen hemorrhoidal tissue. Further, as a result of additional muscle strain during defecation resulting from the physical movement of the fecal mass through the already swollen and inflamed tissue, herniation of the anal walls frequently results. Moreover, the excretory tract is the site of numerous organisms that are infectious and that infiltrate the anal cavity herniations. These infiltration further damages already damaged tissue and aggravate the healing process. If left untreated hemorrhoids often worsen and require surgery to remove the diseased hemorrhoidal tissue.

The common factor between gastrointestinal ulcers and hemorrhoids is the laceration of an internal mucous membrane that gets infected, keeps getting insulted by internal secretions, all of which compound the difficulties in healing such wounds. There exists a need therefore to devise a composition that will safe to ingest, provide reliable relief from pain, have antibacterial activity and above all have an active role in the initiation of wound healing. Herbal natural medicine provides many opportunities whereby a safe and proper combination of herbs or other natural ingredients prepared in accordance with techniques that extract only desirable portions of the ingredient can yield an effective pharmaceutical product. In this invention, three herbs and an animal tissue widely used in the Chinese medicine and one herb which is not very popular in the Chinese medicine are combined to create a potent and safe formulation for the treatment of gastrointestinal ulcers and hemorrhoids.

Many remedies are known for the alleviation of these symptoms. Most of the remedies in the art have varying degrees of success, and few remedies have been successful in substantially reducing or completely eliminating hemorrhoidal symptoms without undesirable side effects. The prior art has suggested the therapeutic utility of certain unknown compounds of various herbs. In particular, U.S. Pat. No. 481,815 to Page et al. describes an herbal composition comprised of *Acacia farnesiana, Acacia constricta,* and *Flourensia cornnua;* U.S. Pat. No. 272,138 to Holder discloses an ointment comprising *Anthemis cotula;* U.S. Pat. No. 3,781,424 to Ponvert discloses a composition comprising extracts of *Capsicum annum;* U.S. Pat. No. 1,383,896 to Wood et al. discloses an ointment comprising extracts of Gnaphalium, Balm of Gilead buds, and elder bark; U.S. Pat. No. 1,890,596 to Zographos discloses an ointment comprising extracts of powdered calomel and green tansy weed; U.S. Pat. No. 3,935,310 to Homan discloses a composition comprising extracts of *Celastrus scandens;* U.S. Pat. No. 4,761,285 to Vasiliou et al. discloses a composition comprising extracts of Leptandra root, chick peas and grape seeds; U.S. Pat. No. 3,464,972 to Rocher discloses a composition comprising extracts of *Ficaria ranunculus;* and, U.S. Pat. No. 5,002,767 to Masse discloses a composition comprising extracts of the Resedaceae family. Yet none of these compositions involve the use of the combination of the ingredients described in the present invention.

Treatments of hemorrhoids have tended to focus on topical applications of creams and lotions and suppositories having medicaments therein that have sought to relieve itching (*Pruritis ani*) and/or inflammation. The efficacy of the prior art treatments in relieving or curing a variety of symptoms is uncertain. Exemplary such creams or lotions are described in: U.S. Pat. No. 4,169,143 to Haimowitz, which discloses a treatment of hemorrhoids with compositions comprising Vitamin E; U.S. Pat. No. 3,062,716 to Montandraud which discloses a treatment of hemorrhoids with compositions comprising heparin; U.S. Pat. No. 3,534, 102 to Waldstein, which discloses a treatment of hemorrhoids with compositions comprising reaction products of elemental iodine and alkoxylated alkylamine oxides; U.S. Pat. No. 3,594,473 to Hunger et al. which discloses a treatment of hemorrhoids with compositions comprising reaction products of ethyl-3,5,6-tri-O-benzyl-D-glucofuranoside; U.S. Pat. No. 5,266,571 to Amer discloses a treatment of hemorrhoids with 5-hydroxytryptamine antagonist; U.S. Pat. No. 4,945,084 to Packman discloses a treatment of hemorrhoids with disaccharide polysulfate-aluminum compounds; U.S. Pat. No. 4,118,480 to Williams discloses a treatment of hemorrhoids with a mixture of compounds; U.S. Pat. No. 4,202,825 to Taya discloses a treatment of hemorrhoids with a derivative of quercetin; U.S. Pat. No. 4,265,887 to Breskman discloses a treatment of hemorrhoids with a mixture of vitamins; U.S. Pat. No. 4,626,433 to Gold discloses a treatment of hemorrhoids with a salve comprising aluminum potassium sulfate, linseed oil, methanol, camphor and pure petroleum jelly; U.S. Pat. No. 4,985,257 to Verde discloses a treatment of hemorrhoids with a composition comprising cream of tartar; U.S. Pat. No. 5,196,405 to Oakman discloses a treatment of hemorrhoids with a composition comprising disaccharide polysulfate-aluminum compounds; U.S. Pat. No. 5,234,914 to Gallina discloses a treatment of hemorrhoids with a composition comprising hyaluronic acid; and, U.S. Pat. No. 5,403,867 to Okumura discloses a treatment of hemorrhoids with a composition having antipruritic properties.

The U.S. Pat. No. 6,048,533 to Nguyen is for an invention that relates administration of an effective amount of turmeric for the treatment of various health ailments and also as a food supplement to promote health and vitality. The turmeric is especially useful for the treatment of skin disorders, such as acne, when administered orally. It can also be applied topically as a whitened or bleached composition. It can also be used to treat liver and stomach disorders, skin discoloration, constipation, and hemorrhoids.

The U.S. Pat. No. 5,869,059 to Garza is for an anti-hemorrhoidal composition, tea, and kit containing tea bags including, in combination, a first herb of the genus Equisetaceae and a second herb of the Generic Juliania, family Julianiaceae, genus *Amphipterygium adstringens* (also known as "Cuachalalate.").

The U.S. Pat. No. 5,591,436 to Pruthi for a composition for a dietary supplement for use in treating hemorrhoids includes: 60% to 95% Indian Barberry by weight; 4.8% to 38% Nagkesar by weight; and 0.2% to 2% Margosa Tree Leaves by weight.

The U.S. Pat. No. 5,562,906 to Terry et al., is for a method for the treatment of vascular disorders where bark or berries of the species *Xanthoxylum clavaherculis* L and *Xanthoxylum americanum* Hill, both of the yellow wood tree family, both containing the compound xanthoxylum, are employed for the treatment of hemorrhoids and other membrane and capillary disorders of the veins and arteries. Improved strength and flexibility of the veins, arteries and their constituent structures is obtained.

However, all of the topical preparations have the drawback of further agitating already swollen and inflamed tissue by the manual application of the medicament. Further, there may be hemorrhoids located deep within the anal rectal cavity that are inaccessible from the exterior thereof for the topical application of medicaments. Hence, there exists a need for an edible composition that can be taken orally for the relief and treatment of internal hemorrhoids and hemorrhoidal symptoms. Additionally, and optionally, there is a need to apply a preparation locally where such treatment is possible without producing irritation to hemorrhoids. It is an object of the present invention to solve the problems in the art.

DETAILED DESCRIPTION

The invention described here comprises a mixture of four herbs and one animal tissue, which are extracted in its preferred embodiment by soaking in 95% Ethanol (USP grade) for a period of two weeks while stirring in closed containers and then straining and filtering the extract. Other extraction procedures, such as, but not limited to, include, extracting in water, water-alcohol mixture, organic solvents or oils. Each extract is standardized according to its marker compound(s) and factored into final calculation of the amount of extract used for the manufacturing of final preparation. The extracts corresponding to about 2%, of the original powdered form of the herb or animal source are mixed together in a stainless steel tank with vacuum and heating implementation and then an amount of vegetable oil, preferably canola oil and the preparation mixed for a suitable time such as 10 minutes. Vacuum is then applied while heating the preparation to 40° C. to remove alcohol, leaving a residue of alcohol not more than one percent in the final preparation. The oil mixture is then filtered through muslin cloth to remove any suspended particles and packaged in soft gelatin capsule, each capsule containing about 1 G of oil mixture. For the preparation of an ointment, the quantity of vegetable oil added to preparation is reduced by 8% and while the preparation is still hot, pharmaceutical grade wax in the amount equivalent to final preparation composition of 8% is added and the mixture stirred gently for about 5 minutes at elevated temperature and then allowed to cool in appropriate containers such as laminated plastic tubes or laminated aluminum tubes or jars (laminated plastic, laminated metal or glass). The quantity of wax can be adjusted to provide a consistency of ointment suitable for rectal administration.

Huangqin (*Scutellaria baicalensis* Georgi) used in the invention is selected but not limited to one or more from the group of *Scutellaria viscidula* Bge, *Scutellaria amoena* C. H. Wright, *Scutellaria rehderiana* Diels, *Scutellaria ikonnikovii* Juz, *Scutellaria likiangensis* Diels and *Scutellaria hypericifolia* Levl of Labiatae Family. The root or radix is used. (A Dictionary of Chinese Materia Medica, Shanghai Science and Technology Press, 1988, pages 2017 to 2021). It is known to have antilipidemic, anticoagulant, antithrombotic, antiallergant, vasodilatation and antibacterial properties.

Huangbo (*Phellodendron amurense* Rupr) used in the invention is selected but not limited to from one or more groups of Phellodendron chinese Schneid, Plellodendron chinense Scheid var. glabriusculum Schneid, Phellodendron chinense Schneid var. omeiense Huang, Phellodendron Schneid var. yunnanense Huang and Phellodendron chinense Schneid var. falcutum Huang. The bark or cortex is used. (A Dictionary of Chinese Materia Medica, Shanghai Science and Technology Press, 1988, pages 2031 to 2035). Phellendori contains berberine and palmitine alkaloids, polysacchcharides; it is immunosuppressive, bactericidal, anti-inflammatory, bile secretion stimulant, affects gastric secretions and has antiacne properties. The U.S. Pat. No. 6,030,978 to Kim, et al., is for an antifungal formulation comprising photoberberine derivatives and salts thereof.

Huanglian (*Coptis chinensis* Franch) used in the invention is selected but not limited to one or more from the group of *Coptis deltoidea* C. Y. Cheng et Hsiao, *Coptis omeiensis* (Chen) C. Y. Cheng, and *Coptis teetoides* C. Y. Cheng of Ranunculaceae Family. The root is used. (A Dictionary of Chinese Materia Medica, Shanghai Science and Technology Press, 1988, pages 2022 to 2030). Huanglian also contains berberine (see above).

Earthworm also called Dilong (earth dragon) is selected but not limited to one or more from the group of *Pheretima aspergillum* (*E. Perrier*) and *Allolobophora caliginosa* trapezoides (Ant. Duges). The whole worm dried or fresh is used. (A Dictionary of Chinese Materia Medica, Shanghai Science and Technology Press, 1988, pages 2111 to 2114). It is known to have antispasmodic, antithrombotic activity. The U.S. Pat. No. 5,128,148 to Ishii, et al., is for a process for the production of dried earthworm powder and antihyperlipemic, antidiabetic, antihypertensive and antihypotensive preparations containing dried earthwork powder as active ingredient. The U.S. Pat. No. 5,186,944 to Ishii, et al., is for a therapeutic medicament for thrombosis prepared by treating live earthworm into a powdery form.

Cactus is selected but not limited to one or more from the group of plant of *Opuntia ficus* indica (Cactacea family). Other species and varieties of Opuntia genus of the Cactaceae family are included here by reference. The reported pharmacologic properties of Opuntia include: analgesia, anti-inflammatory, antiulcerogenic, antioxidative, affecting activity of aromatase and reductase, free radical scavenger, antiviral, lowering LDL cholesterol levels, glucose-6-phosphatase and fructose-1,6-diphosphatase activity, antidiabetic, a rich source of biologically active alkaloids and other nutritional elements often considered essential for tissue growth. The U.S. Pat. No. 5,736,584 to Kunkel is for an insect repelling composition comprising mineral oil cactus extract made from the leaves and stem of the Prickly Pear cactus. The U.S. Pat. No. 5,747,462 to Feuntes relates to the area of pharmacology; its objective is to solve the technical problem of inflammation, pain, pruritus and local hyperthermia in human beings and animal species. The composition and the subcompositions thereof are obtained from plants of the family Cactaceae the main methodological steps being a set of processes: production, purification, physicochemical quantification, biotherapeutic evaluation, biopharmaceutical formulation and molecular identification. From the molecular identification a set of molecules is recognized, comprising carbohydrates and an aromatic amine.

Of interest to this invention is the U.S. Pat. No. 5,405,608 to Xu for an invention that relates to an external pharmaceutical preparation used for treating thermal injuries of warm-blooded mammals and human. It is composed of 3 to 15% by weight of beeswax and 85 to 97% by weight of sesame oil extract of Huangqin, Huanglian, Huangbai, earthworm and poppy capsule. In the sesame oil extract, prepared by scorching the herbal mixture at high heat, each of Huangqin, Huanglian, Huangbai, earthworm and poppy capsule is in an amount of 2 to 10 weight percent based upon the total weight of sesame oil. This invention also indicates beeswax as its essential component, which forms a matrix that acts to debride the skin.

The application of the pharmaceutical preparation of the present invention made from natural ingredients. Many of the ingredients used in the formulation of preparation are described and characterized in the Chinese Pharmacopoeia (Pharmacopoeia of The People's Republic of China, English Edition 1994, Volume I. The Pharmacopoeia Commission of PRC, Beijing, China: Cortex Phellodendri (Huangbo), p 33; Rhizoma Coptidis (Hunaglian), p187; Radix Scutellariae (Hunagqin), p 170; Pheretime (Dilong), p 128) and the specifications of these ingredients are hereby included by reference in this patent application. *Opuntia ficus* indica is not included in the Chinese Pharmacopoeia. The source material for this plant includes the entire plant including flowers, dried and powdered. Canola oil is the oil from low erucic acid variety of rapeseed plant and is widely used for everyday cooking. The specifications include: free fatty acid maximum 0.05% as oleic acid, peroxide value 1.0 meq/Kg maximum, AOM (OSI) 12 hours min to 100 meq/Kg, iodine value 110–126. The choice of canola oil is not material to this invention. Any vegetable oil, preferably those high in natural sterols, can be used. Wax represents any solidifying agent, which may include natural or synthetic waxes, or other ingredients that impart the preparation a consistency suitable for rectal administration. The composition described above prepared using the method prescribed results in a product that actively heals wounds and lacerations of mucous membrane. The composition described here is also effective in inhibiting the growth of *Helicobacter pylori,* the microorganism most often listed as responsible for the propagation of many gastric and duodenal ulcers. Furthermore, the pharmaceutical preparation of the invention described here relieves pain, provides soothing effect and upon repeated use, has the ability to heal the wounds of mucous membranes.

The invention described here is taken orally for the treatment of gastrointestinal ulcers and hemorrhoids in the dose of 2–4 soft gelatin capsules 2–4 times per day for at least one week; in chronic cases, longer therapy may be needed. For the treatment of hemorrhoids, the ointment preparation as described above is optionally but additionally applied to rectal area using a suitable applicator 3–4 times per day for a period ranging from one week to 12 weeks to complete heal the hemorrhoids. The dose suggested here is for reference purpose only and so is the proposed regimen.

Being an all-natural product, it is safe to consume it at higher doses and specific titration of dosing is needed, as a clinician or others expert in the art of treatment would readily master using the preparation described here.

What is claimed is:

1. An oral composition for the amelioration or treatment of gastrointestinal ulcers and hemorrhoids comprising effective amounts of extracts of Huanglian, Huangqin, Huangbo, Pheretima, and Opuntia.

2. A rectal composition for the amelioration or treatment of hemorrhoids comprising effective amounts of extracts of Huanglian, Huangqin, Huangbo, Pheretima and Opuntia.

3. The composition in claim 1, wherein the composition is administered as a liquid, tablet, gelatin capsule, suspension or liposome.

4. The composition of claim 2, wherein the composition is administered as an suppository patch or ointment.

5. THe composition of claim 1, wherein the gastrointestinal ulcers comprise lesions of the mucous membrane of the GI tract.

6. The composition of claims 1 or 2, wherein the composition is combined with other active drugs for the amelioration or treatment of gastrointestinal ulcers and hemorrhoids.

* * * * *